(12) United States Patent
Viola

(10) Patent No.: US 7,695,482 B2
(45) Date of Patent: Apr. 13, 2010

(54) LIGATION CLIP APPLIER AND METHOD

(75) Inventor: Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 11/983,268

(22) Filed: Nov. 8, 2007

(65) Prior Publication Data

US 2008/0065119 A1  Mar. 13, 2008

Related U.S. Application Data

(62) Division of application No. 10/426,616, filed on Apr. 29, 2003, now Pat. No. 7,316,693.

(60) Provisional application No. 60/376,424, filed on Apr. 29, 2002.

(51) Int. Cl.
*A61B 17/10* (2006.01)

(52) U.S. Cl. ............................ 606/139; 606/157

(58) Field of Classification Search ............... 606/151, 606/157, 158, 139, 142
See application file for complete search history.

(56) References Cited

U.S. PATENT DOCUMENTS

| | | | |
|---|---|---|---|
| 3,802,437 A | 4/1974 | Kees, Jr. | |
| 4,791,707 A | 12/1988 | Tucker | |
| 4,796,627 A | 1/1989 | Tucker | |
| 4,932,955 A | 6/1990 | Merz et al. | |
| 4,935,026 A | 6/1990 | McFadden | |
| 5,030,226 A | 7/1991 | Green et al. | |
| 5,035,692 A | 7/1991 | Lyon et al. | |
| 5,062,848 A | 11/1991 | Frazee et al. | |
| 5,163,945 A | 11/1992 | Ortiz et al. | |
| 5,192,288 A | 3/1993 | Thompson et al. | |
| 5,207,692 A | 5/1993 | Kraus et al. | |
| 5,217,473 A | 6/1993 | Yoon | |

(Continued)

FOREIGN PATENT DOCUMENTS

EP  0346084 A1  12/1989

(Continued)

OTHER PUBLICATIONS

European Search Report for EP 03721976.3-1265 date of completion is Jan. 31, 2008 (3 pages).

(Continued)

*Primary Examiner*—Anhtuan T Nguyen
*Assistant Examiner*—Tuan V Nguyen

(57) ABSTRACT

A torsional ligation clip applier and method of use for endoscopic or laparoscopic vessel occlusion procedures is provided. The ligation clip includes a hub portion and ligation arms for occluding a vessel. Ligation arms are independently rotatable about a common axis that is parallel to the longitudinal axis of the ligation arms. The ligation arms are biased in a first position by a biasing mechanism. The ligation arms of the clip are rotatable through at least one of a plurality of positions wherein it has a larger diameter than an access device. An applier receives at least one ligating clip in a first position and delivers the ligating clip to a vessel in a second position. Occlusion of the vessel occurs when one of the ligation arms is rotated into a third position.

13 Claims, 5 Drawing Sheets

U.S. PATENT DOCUMENTS

| | | | | |
|---|---|---|---|---|
| 5,242,456 | A * | 9/1993 | Nash et al. | 606/142 |
| 5,246,450 | A | 9/1993 | Thornton et al. | |
| 5,290,299 | A | 3/1994 | Fain et al. | |
| 5,300,081 | A | 4/1994 | Young et al. | |
| 5,340,360 | A | 8/1994 | Stefanchik | |
| 5,342,373 | A | 8/1994 | Stefanchik et al. | |
| 5,354,304 | A | 10/1994 | Allen et al. | |
| 5,382,253 | A | 1/1995 | Hogendijk | |
| 5,382,255 | A | 1/1995 | Castro et al. | |
| 5,409,498 | A | 4/1995 | Braddock et al. | |
| 5,431,668 | A | 7/1995 | Burbank, III et al. | |
| 5,431,669 | A | 7/1995 | Thompson et al. | |
| 5,439,468 | A | 8/1995 | Schulze et al. | |
| 5,449,365 | A | 9/1995 | Green et al. | |
| 5,474,567 | A | 12/1995 | Stefanchik et al. | |
| 5,514,149 | A | 5/1996 | Green et al. | |
| 5,542,949 | A | 8/1996 | Yoon | |
| 5,547,474 | A | 8/1996 | Kloeckl et al. | |
| 5,601,573 | A | 2/1997 | Fogelberg et al. | |
| 5,607,436 | A | 3/1997 | Pratt et al. | |
| 5,653,720 | A | 8/1997 | Johnson et al. | |
| 5,665,097 | A | 9/1997 | Baker et al. | |
| 5,681,330 | A | 10/1997 | Hughett et al. | |
| 5,700,271 | A | 12/1997 | Whitfield et al. | |
| 5,720,756 | A | 2/1998 | Green et al. | |
| 5,725,537 | A | 3/1998 | Green et al. | |
| 5,772,673 | A | 6/1998 | Cuny et al. | |
| 5,792,150 | A | 8/1998 | Pratt et al. | |
| 5,824,008 | A | 10/1998 | Bolduc et al. | |
| 5,830,221 | A | 11/1998 | Stein et al. | |
| 5,833,700 | A | 11/1998 | Fogelberg et al. | |
| 5,868,759 | A | 2/1999 | Peyser et al. | |
| 5,897,565 | A * | 4/1999 | Foster | 606/158 |
| 5,904,693 | A | 5/1999 | Dicesare et al. | |
| 5,928,253 | A * | 7/1999 | Sherman et al. | 606/151 |
| 5,964,772 | A | 10/1999 | Bolduc et al. | |
| 6,193,732 | B1 * | 2/2001 | Frantzen et al. | 606/151 |
| 6,226,843 | B1 | 5/2001 | Crainich | |
| 6,251,117 | B1 | 6/2001 | Kringel et al. | |
| 6,296,656 | B1 | 10/2001 | Bolduc et al. | |
| 7,316,693 | B2 * | 1/2008 | Viola | 606/139 |
| 2002/0111642 | A1 | 8/2002 | Wright et al. | |
| 2003/0199888 | A1 | 10/2003 | Lutze et al. | |

FOREIGN PATENT DOCUMENTS

| | | |
|---|---|---|
| GB | 2161206 A | 1/1986 |
| WO | WO 89/-05124 A | 6/1989 |
| WO | WO 99/13780 A | 3/1999 |

OTHER PUBLICATIONS

European Search Report. Application No. EP 08 16 1810.

* cited by examiner

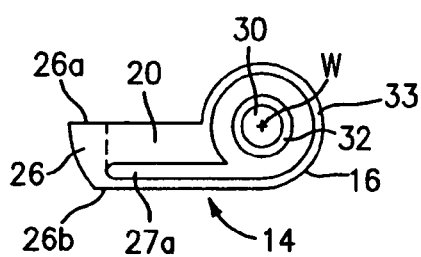
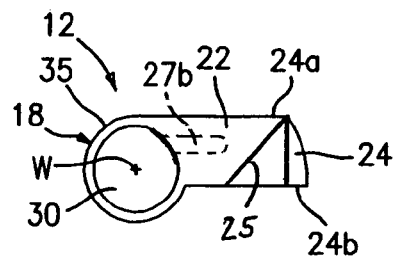
FIG. 4A  FIG. 4B
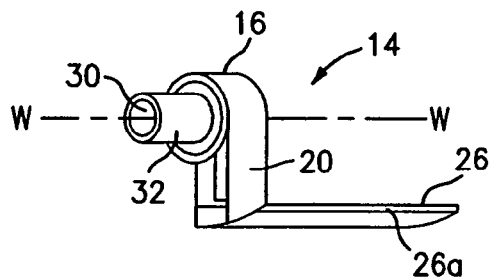
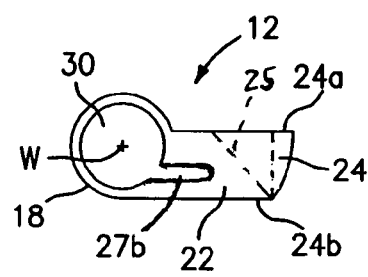
FIG. 5A  FIG. 4C
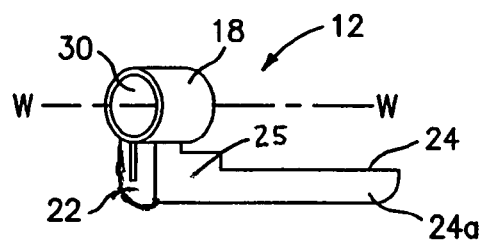
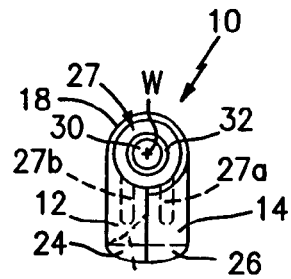
FIG. 5B  FIG. 5C
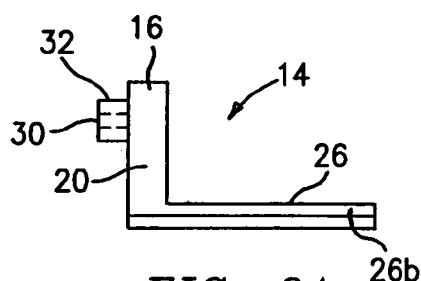
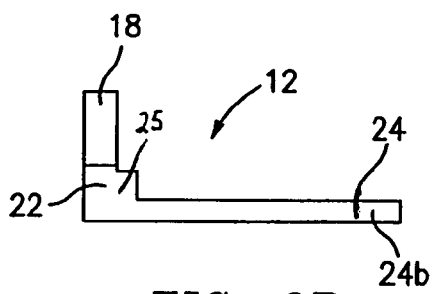
FIG. 6A  FIG. 6B

LIGATION CLIP APPLIER AND METHOD

CROSS REFERENCE TO RELATED APPLICATIONS

This application is a divisional of U.S. application Ser. No. 10/426,616, filed Apr. 29, 2003, now U.S. Pat. No. 7,316,693, which, in turn claims priority from, and the benefits of, U.S. provisional application Ser. No. 60/376,424 filed Apr. 29, 2002, the entire contents of which are incorporated by reference in their entirety.

BACKGROUND

1. Technical Field

The present disclosure relates to ligating clips, and to devices and methods for applying the same in surgical procedures. More specifically, the present disclosure relates to torsionally biased surgical ligating clips suitable for clamping blood vessels and ducts during laparoscopic or endoscopic surgery.

2. Background of Related Art

During surgical procedures, procedures frequently require the temporary or permanent occlusion of vessels to prevent the leakage of fluids (e.g. blood) through incisions made at the surgical site. A broad range of surgical ligating devices and techniques exist for occluding vessels. These include applying surgical ligating clips that are available in a variety of shapes and sizes including spring biased wires and plates. Typically, these devices are stored in a first position wherein the jaws of the clip are biased closed. The applying device opens the jaws of the ligating clip a predetermined distance against the bias of the ligating clip to position the ligating clip about a vessel. The applying device then releases the jaws to allow the bias of the ligating clip to return the jaws of the ligating clip to the closed position and occlude the vessel.

Ligating clips configured for use with applying devices are frequently limited in their application by the distance the jaws can open without permanently deforming the clip. The use of such clips is further limited by the accessibility to the surgical site. For example, only those clips sized to be inserted through an appropriately sized cannula can be used during laparoscopic or endoscopic procedures. In addition, clips having extended jaws can lose the amount of applied bias over time as the tissue shrinks and/or necroses.

Ligating clips for clamping blood vessels and ducts during open and endoscopic (herein understood to include laparoscopic) surgical procedures are well known in the art. The particular dimensions of a ligating clip to be used in an open surgical procedure are not constrained by the size of the access opening to the surgical site. However, during endoscopic surgical procedures access to the surgical site is typically achieved through an access device, such as a cannula, having a limited internal dimension (e.g. a diameter of 15, 10, or 5 mm). Accordingly, ligating clips used during endoscopic surgical procedures must be dimensioned and configured to be admitted to the surgical site through the access device. Because of the dimensional constraints on ligating clips used for endoscopic surgery, currently available ligating clips suffer from several drawbacks. These drawbacks include a smaller or reduced clamp opening, i.e., the distance between opposed clamping members of the ligating clip in the open position, and a difficulty in applying the ligating clips about tissue.

A continuing need exists for a simplified ligating clip having suitable flexibility for application over a range of vessel sizes without excessively deforming and that can maintain pressure on a vessel even when the vessel increases or decreases in size over time.

A continuing need also exists for a ligating clip that can be of a size that facilitates delivery through a cannula of limited internal dimensions, yet can maintain pressure on a vessel even when the vessel increases or decreases in diameter over time.

Accordingly, a need exists for a ligating clip that is suitable for use during endoscopic surgical procedures that has an enlarged clamp opening that can be positioned quickly and easily about tissue. In addition, there is a need for a ligating clip system including an applier and method for applying the ligating clip.

There is also a need for a clip applier that can apply the aforementioned ligating clips and that can be employed through cannulae having internal diameters of 15, 10, or 5 mm.

SUMMARY

This invention is directed to a ligating clip for occluding a vessel including first and second clamping members. Each of the clamping members includes a hub portion with a substantially centrally located throughhole where the hub portions defining a common pivot axis for the hub portions and clamping members, an elongated ligation arm disposed substantially parallel to the common pivot axis, and a hub extension extending between and connecting the hub portion to the ligation arm, the first and second clamping members being pivotably connected by a biasing member such that the clamping members are rotatable about the common pivot axis, and the ligation arms are biased by the biasing member. Each ligation arm can include an elongate vessel clamping surface where the clamping surfaces are biased by the biasing member to engage each other to clamp a vessel therebetween. The biasing member can bias the ligation arms such that in the absence of a vessel therebetween, the clamping surface of one ligation arm contacts at least a portion of the other ligation arm's clamping surface. One of the first and second clamping members can be rotatable relative to the other clamping member through an arc of from about 0° to about 360°, or, less preferably, through an arc of from greater than about 0° to about 360°. Each ligation arm can include a ligation arm abutment surface that is oppositely disposed to each ligation arm's clamping surface and the abutment surfaces of the ligation arms being abuttable with each other. The biasing member can bias the ligation arms such that the ligation arms are rotatable from and amongst a plurality of positions. The biasing member may be a torsion spring. Each ligation arm can be disposed substantially orthogonal to the hub extension to which the ligation arm is connected. One clamping member can have an extension abutment surface that is adapted to abut the hub extension of the opposed clamping member. The throughhole of one hub portion can be defined by the inside surface of a cylindrical wall that defines the common pivot axis, and the outside surface of the cylindrical wall partly defines a portion of a channel for receiving the biasing member therein.

This invention is also directed to a ligating clip system for occluding a vessel including at least one ligating clip having first and second clamping members. Each of the clamping member includes a hub portion with a substantially central throughhole where the hub portions define a common pivot axis, a ligation arm disposed substantially parallel to the common pivot axis, and a hub extension connecting the hub portion to the ligation arm, where the first and second clamping members are pivotably connected such that each is rotatable about the common pivot axis in relation to the other and the ligation arms are biased by a biasing member, and an applier including an elongate tube having a diameter, the elongate tube having a proximal end and a distal end defining a channel therebetween, the channel configured and adapted to receive and restrain the at least one ligating clip, the channel further including an elongate pusher member disposed along a longitudinal axis of the tube, the pusher member being for advancing the ligating clip a predetermined distance distally along the longitudinal axis. The clamping members of the ligation clip can be biased for rotation amongst a plurality of positions. Each ligation arm can include a clamping surface and an opposed abutment surface. The biasing member may be a torsion spring. The system can include an actuation mechanism where the actuation mechanism includes a trigger assembly. The channel can receive and restrain the at least one ligating clip in a first position where the abutment surfaces are in contact with one another. The distal end of the tube can be adapted and configured to contact the clamping assemblies. The biasing member and the distal end of the tube can cooperate to rotate the clamping members of the ligating clip from the first position to a second position as it advances distally from the distal end of the channel wherein the first ligation arm is spaced apart from the second ligation arm. The first and second ligation arms can be substantially parallel to one another in a substantially planar arrangement. The ligation arms can span a distance that is greater than the diameter of the distal end of the elongate tube. The biasing member and the distal end of the tube can cooperate to rotate the clamping members of the ligating clip from the second position to a third position as the ligating clip advances from the channel to the predetermined distance wherein the clamping surfaces are biased by the biasing member to engage one another in a manner sufficient to occlude a vessel therebetween were it placed between the clamping members. The elongate tube can have opposed first and second inserts disposed along at least a portion of the elongate tube where the inserts restrain the ligating clip in the first position inside the elongate tube. The elongate tube can include opposed elongate restraining walls running through at least the distal end of the tube where the opposed restraining walls forming a clip restraining channel, and one of the restraining walls forming a ledge that extends distally from and beyond the distal end of the tube.

This invention is further directed to a method for occluding a vessel including the steps of making an incision in a patient, inserting an access device into the incision, inserting a clip applier into the access device where the applier has a distal end and at least one ligating clip, and the at least one ligating clip has a pair of distally extending ligation arms biased to clampingly engage each other and the clip being in a first position of a plurality of positions, actuating an actuation mechanism located on or in the applier to cause the ligation arms of the ligating clip to rotate to a second position of the plurality of positions where the ligating arms in the second clip position being of a span greater than a diameter of the clip applier, positioning the ligating clip around the vessel, and actuating the actuation mechanism located on the applier to cause the ligating clip to biasedly rotate to a third position of the plurality of positions thereby clampingly engaging and occluding the vessel. The ligating clip in the second position can have a larger outside diameter than the access device. The applier can include a number of ligating clips. The access device can be a cannula. The actuation mechanism can be a trigger assembly. The applier can include opposed first and second inserts disposed along at least a portion of the inside of the elongate tube where at least one of the inserts extending beyond the distal end of the applier and restraining the ligating clip in the second position.

This invention is directed to a clip applier including an elongate tubular member having proximal and distal ends, opposed elongate restraining walls running through at least the distal end of the tubular member where the opposed restraining walls forming a clip restraining channel, and an elongated pusher for pushing a clip through and beyond the distal end of the tubular member. One of the opposed restraining walls can form a ledge that extends distally from and beyond the distal end of the tubular member and the elongated pusher is adapted to push the clip onto the ledge.

BRIEF DESCRIPTION OF THE DRAWINGS

Preferred embodiments of the presently disclosed ligating clip are described herein with reference to the drawings, wherein:

FIG. 4A is a proximal end view of a first clamping member of the ligating clip of FIG. 1;

FIG. 4B is a distal end view of a second clamping member of the ligating clip of FIG. 1;

FIG. 4C is a proximal end view of the second clamping member of the ligating clip of FIG. 1;

FIG. 5A is a perspective view of the first clamping member of the ligating clip of FIG. 1;

FIG. 5B is a perspective view of the second clamping member of the ligating clip of FIG. 1;

FIG. 5C is a proximal end view of the ligating clip of FIG. 1 in the first position;

FIG. 6A is a side view of the first clamping member of the ligating clip of FIG. 1;

FIG. 6B is a side view of the second clamping member of the ligating clip of FIG. 1;

DETAILED DESCRIPTION OF THE PREFERRED EMBODIMENTS

Figure 1:
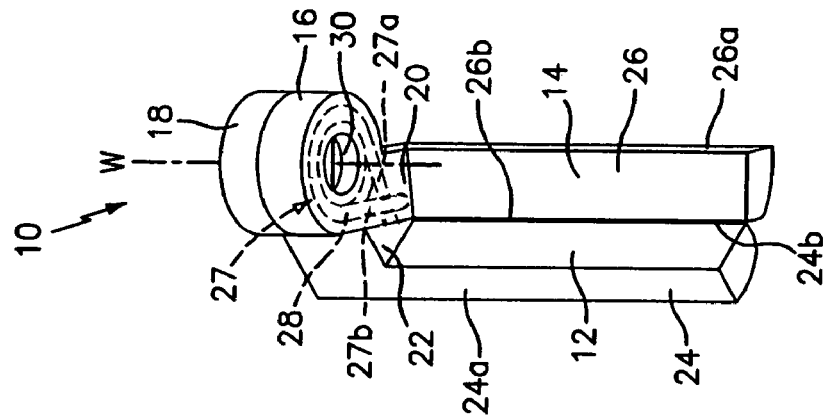
FIG. 1 is a perspective view of an embodiment of a ligating clip in a first position in accordance with the present disclosure.

Preferred embodiments of the presently disclosed ligating clip will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Figure 2:
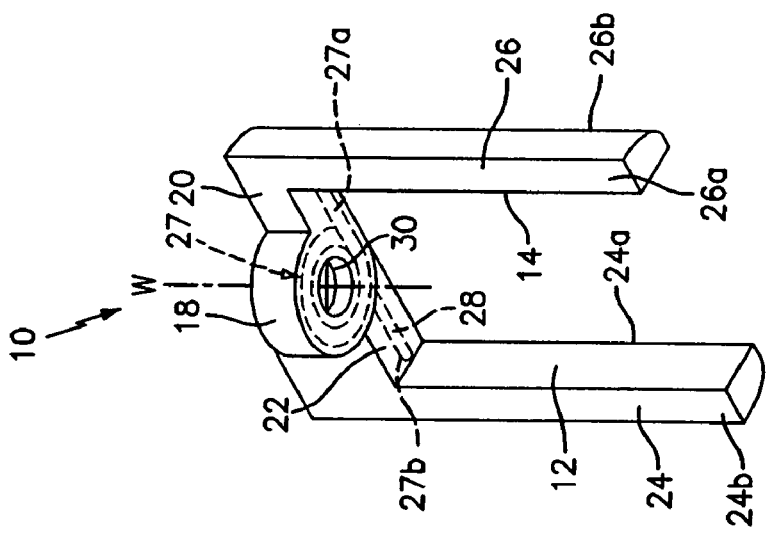
FIG. 2 is a perspective view of the ligating clip of FIG. 1 in a second position.
Figure 3:
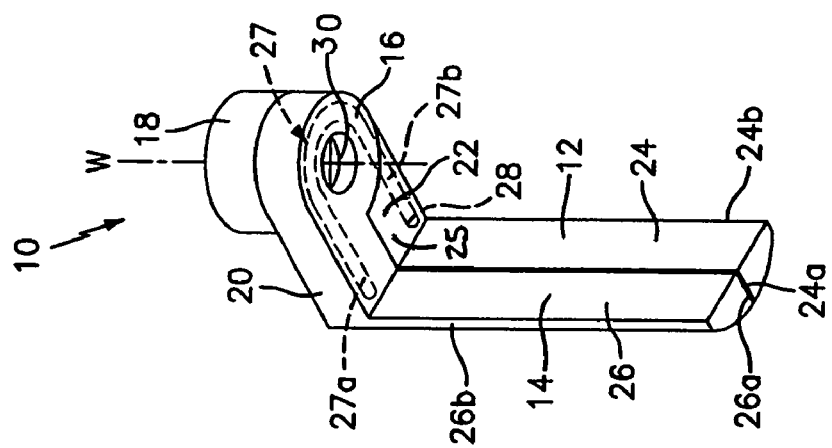
FIG. 3 is a perspective view of the ligating clip of FIG. 1 in a third position.

Referring to FIGS. 1-3, the surgical, or ligating, clip, shown generally as 10, includes first and second clamping members 12, 14. Clamping members 12, 14 include hub portions 16, 18, respectively, hub extensions 20, 22, respectively, and ligation arms 24, 26, respectively. Hub portions 16, 18 are stacked one on top of the other and are pivotal one in relation to the other about a common central pivot axis-W (FIG. 2). Each hub portion 16, 18 has a substantially central throughhole 30. When hub portions 16, 18 are stacked on top of one another, throughholes 30 are aligned with each other and define common central pivot axis-W. Hub extensions 20, 22 project generally radially and outwardly from hub portions 16, 18 and join ligation arms 24, 26 substantially perpendicularly to hub extensions 20, 22 and substantially parallel to, but offset from each other when hub extensions 20, 22 are seen in end views (see FIG. 5C).

Hub portions 16, 18 include channel portions 27a, 27b, respectively, for engaging one end of a biasing member 28. In combination, such as when hub portions 16, 18 are aligned and stacked one on top of the other or behind the other, as shown in FIG. 5C, channel portions 27a, 27b form the terminal end portions of a channel 27 that is configured and dimensioned to receive biasing member 28, preferably a torsion spring (not shown). Each channel portion 27a, 27b may include a shoulder or a recess formed within each hub portion 16, 18 to receive or restrain the terminal ends of biasing member 28. Biasing member 28 is positioned for rotating clamping members 12, 14 in relation to each other about pivot axis-W. Preferably, one of clamping members 12, 14 is independently rotatable in relation to the other over an arc of from about 0°, less preferably from greater than about 0°, to about 360° (less than 360°, because of the width of one ligation arm). Alternately, other channel portions are envisioned, for example, a groove for receiving at least a portion of the terminal end of biasing member 28, or a hole for receiving the terminal end of biasing member 28.

Each ligation arm 24, 26 has an abutment surface 24a, 26a and a clamping surface 24b, 26b, respectively. Preferably, the thickness of each ligation arm 24, 26 decreases from its abutment surface side 24a, 26a to the clamping surface side 24b, 26b. Alternately, ligation arms 24, 26 may have other configurations, e.g., circular, oval, oblong, triangular, rectilinear, etc. In the first, or fully open, starting position of ligating clip 10, i.e., when clamping members 12, 14 have been rotated against the bias of biasing member 28 into contact with each other, abutment surfaces 24a, 26a abut against one another along ligation arms 24, 26, as shown in FIG. 1.

Ligating clip 10 is shown in a second, or "ready," position in FIG. 2. With clamping member 12 held steady or restrained and clamping member 14 unrestrained, as in FIG. 1, biasing member 28 moves clamping member 14 in a clockwise arc of 180° towards clamping member 12 causing rotation of clamping member 14 about central pivot axis-W. By way of example, which is not shown, if clamping member 14 is restrained and clamping member 12 is unrestrained, biasing member 28 will move clamping member 12 counterclockwise toward clamping member 14. Referring again to FIG. 2, applied force from biasing member 28 causes clamping member 14 to rotate about central pivot axis-W. In a preferred embodiment, in the intermediate, ready position, ligation arms 24, 26 are shown about 180° apart and substantially parallel to one another. FIG. 2 shows ligation arm 26 in transit to the approximate 360° position, restrained at the 180° position. It is contemplated that a ligation arm can be restrained at any rotational position, 180° being preferred because it provides the widest spread of the ligation arms to facilitate placing a vessel therebetween.

FIG. 3 shows ligating clip 10 in the third, or fully closed, ligating, or clamped position, where clamping surfaces 24b, 26b abut against each other. Clamping surfaces 24b, 26b may be provided with an irregular surface, e.g. roughened, patterned, knurled, undulated, protrusions, etc., to enhance gripping and/or clamping of tissue. Biasing member 28 maintains clamping surfaces 24b, 26b in the abutting relationship shown in FIG. 3.

By rotating clamping members 12, 14 about pivot axis-W and against the bias of biasing member 28 until abutment surfaces 24a, 26a are in contact with one another, ligating clip 10 will be back in the first, or fully open, position (see FIG. 1). If clamping members 12, 14 are released simultaneously (i.e. neither clamping member 12, 14 is restrained), biasing member 28 imparts rotational force to each clamping member 12, 14 that will cause clamping members 12, 14 to initially rotate away from each other about pivot axis-W. Since neither member is being restrained, clamping members 12, 14 will both rotate through the second, or ready, position (see FIG. 2) where they are about 180° apart and substantially parallel to one another. Biasing member 28 continues to apply biasing forces that cause the continued rotation of clamping members 12, 14 about pivot axis-W until clamping surfaces 24b, 26b are in contact with one another, thereby defining the third, or clamped, position of ligating clip 10 (see FIG. 3).

Ligating clip 10 is preferably formed from surgical grade plastics, although the biasing member may be formed from a surgical grade metal. Alternately, the ligating clip may be formed from any material suitable for surgical use including metals, plastics, ceramics, etc. Ligating clips can be comprised of biodegradable or biological material.

Detailed views of the components of ligating clip 10 are illustrated in FIGS. 4A-4C. First, with reference to FIG. 4A, a proximal end view of ligating clip 10 is shown, detailing the structure of first clamping member 14. As previously discussed, clamping member 14 includes hub portion 16 having a cylindrical wall 32 defining throughhole 30 that is centrally disposed in hub portion 16 and whose central axis is aligned with central pivot axis-W. Hub portion 16 includes a peripheral wall 33 that surrounds cylindrical wall 32. The two walls together generally defining an annular channel 27 (dashed lines in FIG. 1) having a tangential terminal end portions including channel portion 27a (dashed lines in FIG. 1) in hub portion 16 of first clamping member 14 and channel portion 27b (dashed lines in FIG. 1) in hub portion 18 of second clamping member 12. Abutment surface 26a and clamping surface 26b are on opposing sides of first clamping member 14, while ligation arm 26 is connected to hub extension 20 in an orthogonal arrangement.

FIG. 4B shows a distal end view and FIG. 4C shows a proximal end view of second clamping member 12. Second clamping member 12 includes hub portion 18 that has a circular configuration, thereby defining large throughhole 30 that receives cylindrical wall 32 of first clamping member 14. A channel portion 27b is in communication with throughhole 30 and extends, preferably as a tangential groove or slot, internal to hub extension 22. Abutment surface 24a and clamping surface 24b are on opposing sides of second clamping member 12, while ligation arm 24 is connected to hub extension 22 in an orthogonal arrangement. FIG. 4B shows an angled or diagonal abutment wall 25 adjoining ligation arm 24 and hub extension 22 for abutting hub extension 20 of clamping member 14.

FIGS. 5A and 5B show perspective views of first clamping member 14 and second clamping member 12. In FIG. 5A, first clamping member 14 includes hub portion 16. Disposed in hub portion 16 is cylindrical wall 32 that extends beyond the plane of hub portion 16. Cylindrical wall 32 is disposed in the center of hub portion 16, defines throughhole 30, and is adapted for sliding engagement or coupling with hub portion 18 of second clamping member 12. Clamping member 12, as shown in FIG. 5B, includes hub portion 18 that defines throughhole 30 and that is configured and dimensioned for peripherally encompassing cylindrical wall 32 of clamping member 14. Hub extensions 20, 22 are connected to hub portions 16, 18 respectively and extend preferably generally radially outward from hub portions 16, 18, and substantially parallel to the plane defined by the distal surfaces of respective hub portions 16, 18. Ligation arms 24, 26 extend perpendicularly and distally from the distal walls of hub extensions 20, 22. Abutment surfaces 24a, 26a are adapted for contact with each other along at least a portion of, preferably their entire length.

FIG. 5C shows a proximal end view of the assembled clamping members 12, 14, in the first, or closed, position. The proximal and distal faces of hub portions 16, 18 are preferably parallel to the proximal and distal faces of hub extensions 20, 22. Ligation arms 24, 26 communicate orthogonally with hub extensions 20, 22 and are disposed generally parallel to pivot axis-W. Peripheral wall 33 of hub portion 16 surrounds cylindrical wall 32 to form a portion channel 27 in hub portion 16. Peripheral wall 35 of hub portion 18 has the same diameter and thickness as peripheral wall 33 of hub portion 16, and together the hubs form channel 27 for biasing member 28 (not shown). Clamping surfaces 24b, 26b are disposed on the outer edges of ligation arms 24, 26 (see also FIGS. 6A and 6B).

Figure 7:
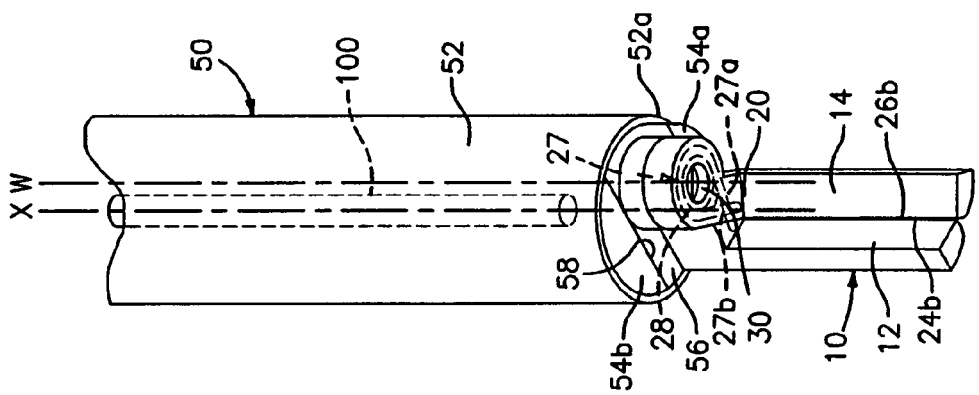
FIG. 7 is a perspective view, with parts broken away, of an embodiment of an applier having a ligating clip in the first position in accordance with the present disclosure.
Figure 8:
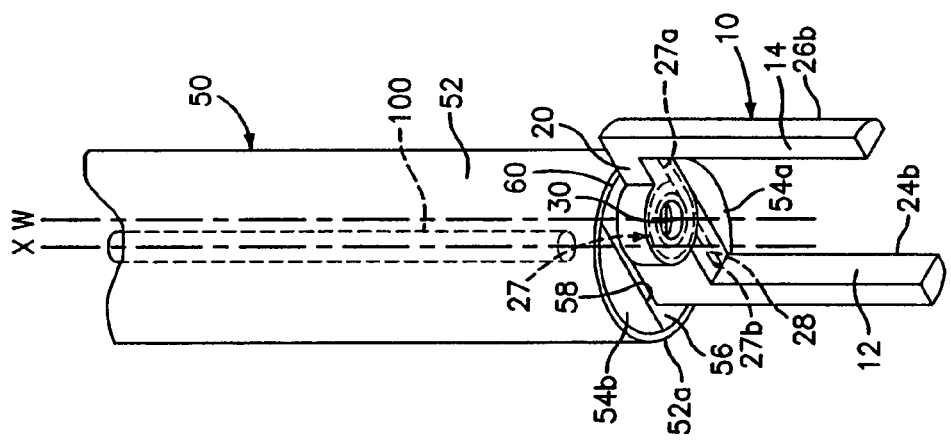
FIG. 8 is a perspective view, with parts broken away, of the applier and ligating clip of FIG. 4 in the second position.
Figure 9:
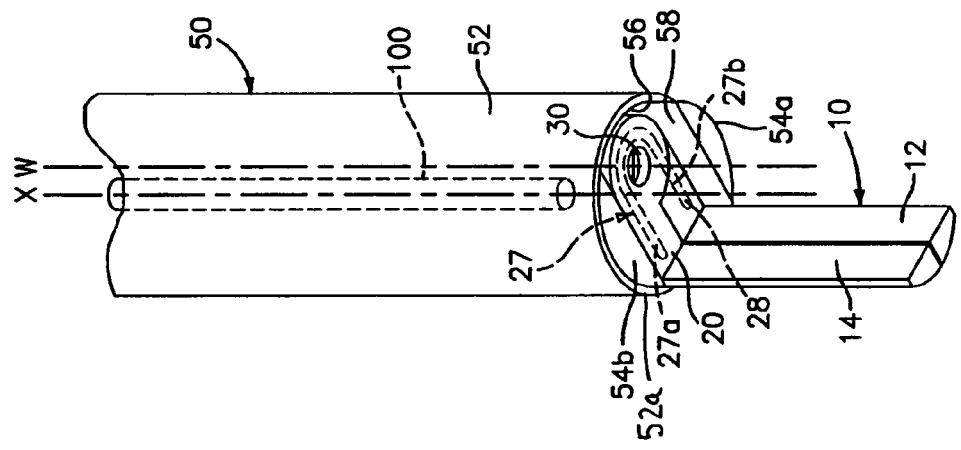
FIG. 9 is a perspective view, with parts broken away, of the applier and ligating clip of FIG. 4 in the third position.

FIGS. 7-9 show a ligating clip system, i.e. a clip applier and clip, where ligating clip 10 is being applied to a surgical site using an applier 50 having a longitudinal axis-X and preferably a cylindrical body 52 having a pair of spaced inserts 54a, 54b. Inserts 54a, 54b can be generally semi-spherical but, as shown, preferably are arcuate segments of a circle (i.e. formed by a secant). The internal wall of cylindrical body 52 and the secants of inserts 54a, 54b define a channel 56 having flat walls 58 and spherical walls 60. Insert 54a projects, preferably permanently, outwardly from the distal end 52a of cylindrical body 52. Alternately, other channel configurations, or stops, that provide a stop against rotation of hub extensions 20, 22 and thereby prevent relative rotation of arms 24, 26 while ligating clip 10 is positioned within channel 56 are envisioned.

A pusher member 100, shown schematically (in dashed lines) in FIG. 7, is movably positioned within cylindrical body 52. At least one, and preferably multiple, ligating clips 10 (one shown) are positioned in longitudinal alignment within channel 56 of cylindrical body 52 preferably in the first, or fully open, position (FIG. 1) with ligation arms 24, 26 positioned distally of hub portions 16, 18. The distal end of the pusher member 100 is positioned to engage a proximal end portion of ligating clip 10, e.g., the proximal face of hub extension 22 of the proximal-most ligating clip 10. Other engagement, clip ejection, and/or pusher systems know in the art can be employed herein for pushing a proximal clip to eject and apply a distal-most clip.

The proximal end of cylindrical body 52 can be attached directly to, near, or to a remote housing (not shown). An actuation mechanism can be included in the housing and can be operatively coupled to pusher member 100. The actuation mechanism is adapted and configured to distally advance pusher member 100 a predetermined distance for each actuation operation and consequently to distally advance ligating clip 10 the predetermined distance.

Preferably, one complete operation of the actuation mechanism will result in the distal advancement of ligating clip 10 such that hub extension 20 engages or goes beyond the distal end of insert 54a and will result in the occlusion of vessel 90. In order to ensure that only one ligating clip 10 is expelled during one operation of the actuation mechanism, preferably a latch and pawl mechanism (not shown) is provided in the housing. In operation, as the actuation mechanism is operated, pusher member 100 is moved distally through cylindrical body 52 thereby engaging and commencing the advancement of ligating clip 10. Once the actuation mechanism is engaged for operation, the latch and pawl mechanism is configured to prohibit the actuation mechanism from backstroking until the actuation mechanism has been completely cycled and ligating clip 10 has been fully advanced, thereby expelling it from cylindrical body 52. Upon complete operation of the actuation mechanism, the pawl clears the gear teeth (not shown) and the pawl rotates away from the teeth due to a spring biasing (not shown), thereby allowing the actuation mechanism to return to its ready condition.

Upon complete operation of the actuation mechanism, pusher member 100 travels a predetermined distance through cylindrical body 52, causing ligating clip 10 to be advanced a predetermined amount. Preferably, the distance is sufficient for ligating clip 10 to engage and occlude vessel 90, and to distally advance at least one additional ligating clip 10 such that at least a portion of ligation arms 24, 26 are exposed at distal end 52a of cylindrical body 52. Moreover, when the actuation mechanism is only partially operated, the spring-loaded pawl (not shown) operates to hold the actuation mechanism stationary and will continue to function to hold the actuation mechanism stationary until the actuation mechanism has been completely operated. In this way, the advancement of ligating clips 10 is controlled so that only a single ligating clip 10 is expelled at a time.

Figure 10:
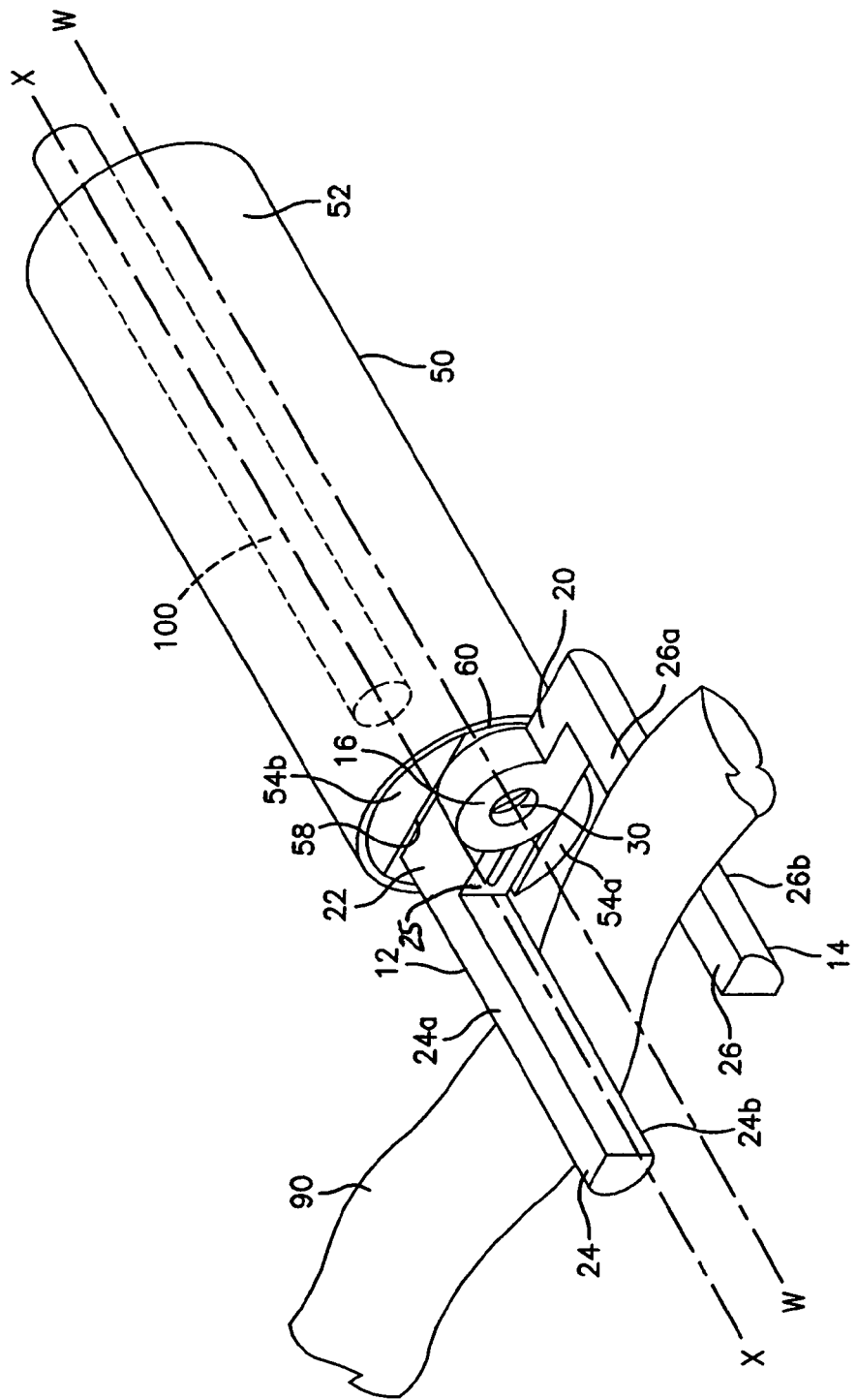
FIG. 10 is a perspective view, with parts broken away, of the applier and ligating clip in the second position surrounding a vessel.

In use, when pusher member 100 is advanced, the distalmost clip 10 is pushed from the distal end 52a of cylindrical body 52. As illustrated in FIG. 7, clamping members 12, 14 of ligating clip 10 extend from cylindrical body 52 but the diameter or width of ligating clip 10 in the first, or fully open, position is less than that of cylindrical body 52. Ligating clip 10 is maintained in the first, or fully open, position (FIG. 1) by the flat sides of inserts 54a, 54b until it is pushed from and beyond the distal end 52a of cylindrical body 52. Referring to FIG. 8, when hub extension 20 passes distally beyond tube body 52 and engages the distal end of insert 54b, the bias of torsion spring 28 (FIG. 2) rotates clamping member 14 approximately 180° in relation to clamping member 12 until hub extension 20 abuts the flat side of distally protruding insert 54a by which and whereat ligating clip 10 is maintained in the second, or "ready" position. Alternately, but less preferably, insert 54a may be positioned or configured to allow clamping member to rotate through greater or lesser arcs of rotation, e.g., 90°, 120°, 270°, etc., to provide any desirable orientation of clamping members 12, 14 in the second, or ready, position. Because the central pivot axis-W of hub portions 16, 18 is offset from the central longitudinal axis-X of cylindrical body 52, in the ready position, the clamp opening, i.e., the distance between clamping surfaces 24b and 26b, is uniquely greater than the diameter of cylindrical body 52. Thus, clamping members 12, 14 can be more easily positioned about tissue 90 to be clamped. (See FIG. 10.)

Figure 11:
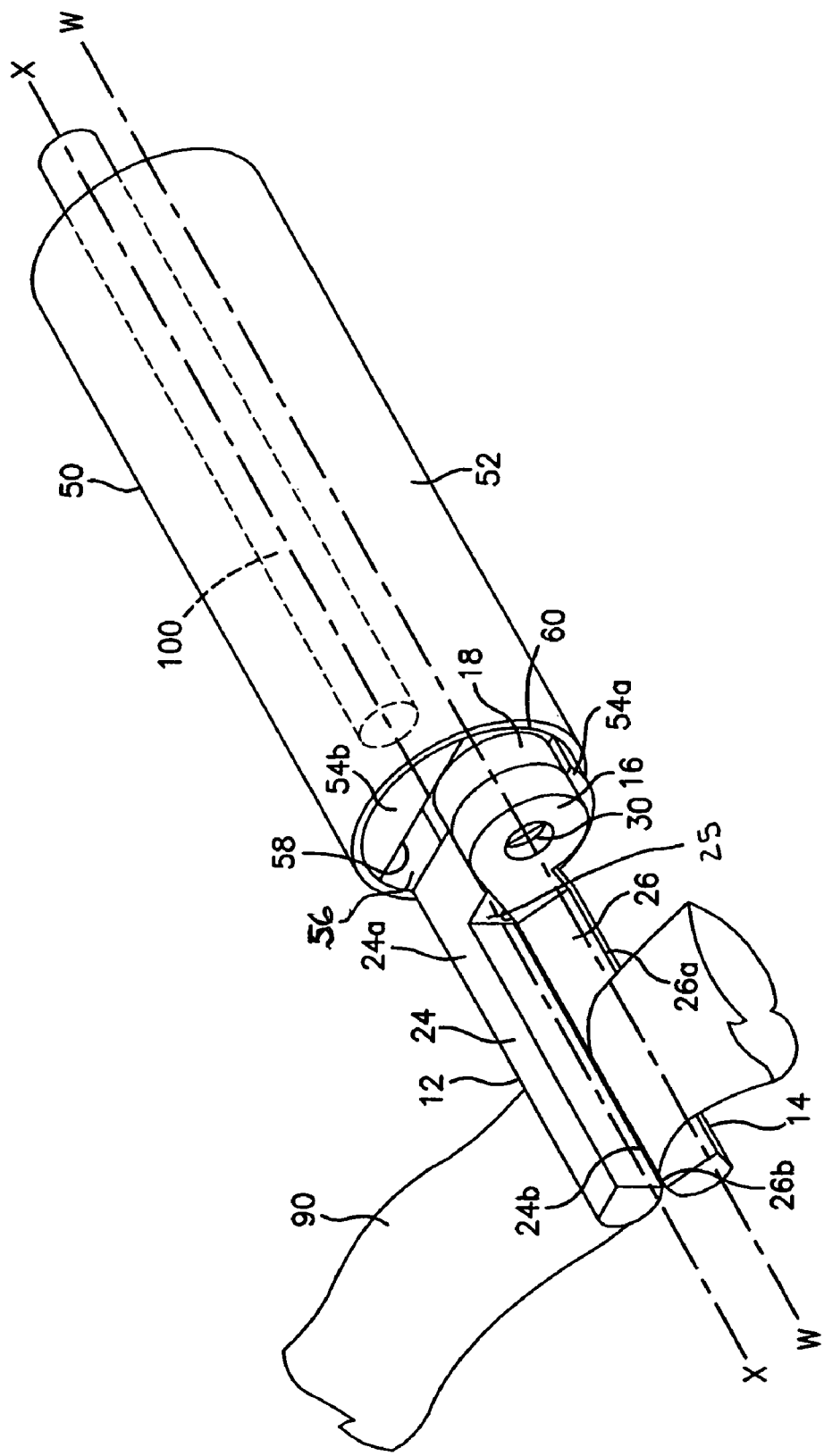
FIG. 11 is a perspective view, with parts broken away, of the applier and ligating clip in the third position with the vessel captured, or occluded, by the clip.

Referring to FIG. 9, when pusher member 100 and, thus, ligating clip 10, is advanced further to the point at which hub extension 20 of hub portion 16 passes distally beyond the distal end of insert 54a, the bias of torsion spring 28 effects rotation of clamp members 12, 14 to the third, closed or clamped, position (FIGS. 9 and 11) in which clamping surfaces 24b, 26b are in abutting relationship (FIG. 9) and tissue 90 is clamped therebetween (FIG. 11). After ligating clip 10 has been clamped about tissue 90, the pusher member (not shown) can be left in place as it has been pushing on the most proximal of a plurality of aligned ligating clips 10 within cylindrical body 52, and, in that case, advanced further to dispense additional ligating clips 10 as and when desired.

It will be understood that various modifications may be made to the embodiments disclosed herein. For example, the configuration of the channel 56 need not be that of a truncated cylinder. Other configurations, which maintain ligating clip 10 in an open, or first, position during delivery of ligating clip 10 through channel 56 of applier 50, are envisioned. Although ligating clip 10 is shown as being constructed of multiple components, it is envisioned that ligating clip 10 could be constructed from a single piece of spring wire or the like. Although no actuating mechanism has been disclosed to effect advancement of pusher member 100, any handle actuator assembly known in the surgical arts for effecting advancement of a pusher member 100 including pistol type actuators having trigger assemblies or in-line handle actuators may be incorporated into applier 50 to effect advancement of pusher member 100. Therefore, the above description should not be construed as limiting, but merely as exemplifications of preferred embodiments. Those skilled in the art will envision other modifications within the scope and spirit of the claims appended hereto.

What is claimed is:

1. A method for occluding a vessel comprising the steps of:
    making an incision in a patient;
    inserting an access device into the incision;
    inserting a clip applier into the access device, the applier having a distal end and at least one ligating clip and defining a longitudinal axis, the at least one ligating clip having a pair of distally extending ligation arms biased to clampingly engage each other and defining a pivot axis extending substantially parallel to the longitudinal axis of the clip applier, the clip being in a first position of a plurality of positions;
    actuating an actuation mechanism located on or in the applier to cause the ligation arms of the ligating clip to rotate about the pivot axis to a second position of the plurality of positions, the ligating arms in the second clip position being of a span greater than a diameter of the clip applier;
    positioning the ligating clip around the vessel; and
    actuating the actuation mechanism located on the applier to cause the ligating clip to biasedly rotate about the pivot axis to a third position of the plurality of positions thereby clampingly engaging and occluding the vessel, wherein the applier further includes opposed first and second inserts disposed along at least a portion of the inside of the elongate tube, at least one of the inserts extending beyond the distal end of the applier and restraining the ligating clip in the second position.

2. The method of occluding a vessel of claim 1, wherein the ligating clip in the second position has a larger outside diameter than the access device.

3. The method of occluding a vessel of claim 2, wherein the applier includes a number of ligating clips.

4. The method of occluding a vessel of claim 1, wherein the access device is a cannula.

5. The method of occluding a vessel of claim 3, wherein the actuation mechanism is a trigger assembly.

6. The method of occluding a vessel of claim 1, wherein the ligation arms of the at least one ligating clip are substantially parallel in the first, second and third positions.

7. The method of occluding a vessel of claim 1, wherein the ligation arms of the at least one ligating clip each include a clamping surface and an opposed abutment surface.

8. The method of occluding a vessel of claim 7, wherein the opposed abutment surface of the ligation arms are in contact with one another when the ligating clip is in the first position.

9. The method of occluding a vessel of claim 7, wherein the clamping surface of the ligation arms are in contact with one another or a vessel when the ligating clip is in the third position.

10. The method of occluding a vessel of claim 1, wherein the ligation arms of the ligating clip rotate from the first position through the second position to the third position.

11. The method of occluding a vessel of claim 1, wherein the pivot axis is substantially parallel the ligating arms.

12. The method of occluding a vessel of claim 1, wherein one of the pair of ligating arms rotates in a first direction about the pivot axis from the first position to the second position.

13. The method of occluding a vessel of claim 12, wherein the one of the pair of ligating arms continues to rotate in the first direction about the pivot axis from the second position to the third position.

* * * * *